US012586683B2

(12) United States Patent
Wei

(10) Patent No.: US 12,586,683 B2
(45) Date of Patent: Mar. 24, 2026

(54) DECISION-MAKING UNDER SELECTIVE LABELS

(71) Applicant: INTERNATIONAL BUSINESS MACHINES CORPORATION, Armonk, NY (US)

(72) Inventor: Dennis Wei, Sunnyvale, CA (US)

(73) Assignee: International Business Machines Corporation, Armonk, NY (US)

( * ) Notice: Subject to any disclaimer, the term of this patent is extended or adjusted under 35 U.S.C. 154(b) by 1125 days.

(21) Appl. No.: 17/381,141

(22) Filed: Jul. 20, 2021

(65) Prior Publication Data

US 2023/0034542 A1      Feb. 2, 2023

(51) Int. Cl.
| | |
|---|---|
| *G06N 20/00* | (2019.01) |
| *G06N 5/045* | (2023.01) |
| *G16H 20/13* | (2018.01) |
| *G16H 50/20* | (2018.01) |

(52) U.S. Cl.
CPC ............. *G16H 50/20* (2018.01); *G06N 5/045* (2013.01); *G06N 20/00* (2019.01); *G16H 20/13* (2018.01)

(58) Field of Classification Search
CPC ........ G16H 50/20; G16H 20/13; G16H 40/67; G16H 50/70; G06N 5/045; G06N 20/00
See application file for complete search history.

(56) References Cited

U.S. PATENT DOCUMENTS

| | | | |
|---|---|---|---|
| 8,001,001 B2 | 8/2011 | Brady et al. | |
| 8,682,724 B2 | 3/2014 | Gonen | |
| 10,635,707 B2 | 4/2020 | Perez et al. | |
| 11,551,117 B1 * | 1/2023 | Malhotra | G06Q 50/26 |
| 2015/0051973 A1 | 2/2015 | Li et al. | |
| 2015/0095271 A1 | 4/2015 | Ioannidis | |
| 2020/0273000 A1 | 8/2020 | Li et al. | |
| 2020/0409983 A1 | 12/2020 | Miller et al. | |
| 2021/0089959 A1 | 3/2021 | Ghosh et al. | |
| 2022/0004863 A1 * | 1/2022 | Park | G16H 50/20 |
| 2022/0402522 A1 * | 12/2022 | Tummala | G06N 20/20 |

OTHER PUBLICATIONS

Kilbertus, Niki et al. "Fair Decisions Despite Imperfect Predictions." arXiv (Cornell University) (2020): n. pag. Web (Year: 2019).*
Bietti, A., Agarwal, A., & Langford, J. (2021). A contextual bandit bake-off. Ithaca: (Year: 2021).*
Casimiro, Maria, et al. "Lynceus: Cost-efficient tuning and provisioning of data analytic jobs." 2020 IEEE 40th International Conference on Distributed Computing Systems (ICDCS). IEEE, 2020. (Year: 2020).*

(Continued)

*Primary Examiner* — Daniel T Pellett
(74) *Attorney, Agent, or Firm* — CHIP LAW GROUP

(57) ABSTRACT

A computer-implemented method of decision-making using selective labels, includes receiving a conditional success probability value of a feature associated with an entity. A confidence value of the received success probability value is received. A parameter value that is a trade-off between a short-term learning and a long-term utility is selected. A decision is rendered to accept or reject the feature associated with the entity according to a machine learning policy.

17 Claims, 11 Drawing Sheets

(56)     References Cited

OTHER PUBLICATIONS

Mell, P. et al., "Recommendations of the National Institute of Standards and Technology"; NIST Special Publication 800-145 (2011); 7 pgs.
Bietti, A. et al., "A Contextual Bandit Bake-off"; airXiv:1802. 040645v5 [stat.ML] (2021); 49 pgs.
Eckles, D. et al., "Thompson Sampling with the Online Bootstrap"; arXiv:1410.4009v1 [cs.LG] (2014); 13 pgs.
Foster, D. et al., "Practical Contextual Bandits with Regression Oracles"; PMLR (2018); 2 pgs.
Kilbertus, N. et al., "Fair Decisions Despite Imperfect Predictions"; Proceedings of the 23rdInternational Conference on Artificial Intelligence and Statistics (AISTATS) 2020; 10 pgs.
Langford, J. et al., "The Epoch-Greedy Algorithm for Contextual Multi-armed Bandits"; Yahoo Research (2008); 8 pgs.

\* cited by examiner

200

201

- Decide using optimal *homogeneous* policy

203

- Compute value function $V^*(\mu(x), v(x); \bar{\gamma}(x))$ by recursion,

Then threshold:

205

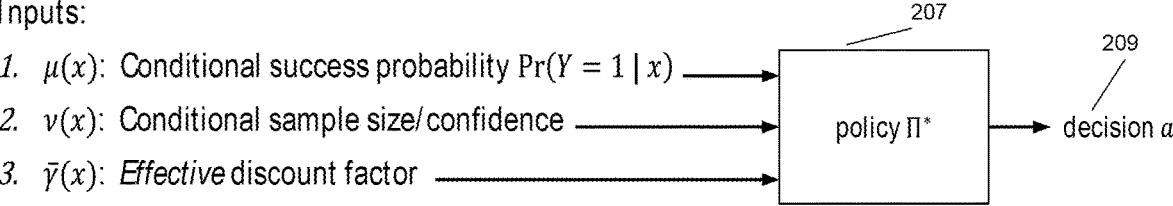

$$\Pi^*(\mu(x), v(x); \bar{\gamma}(x)) = \begin{cases} 1, & V^*(\mu(x), v(x); \bar{\gamma}(x)) > 0 \\ 0, & V^*(\mu(x), v(x); \bar{\gamma}(x)) \leq 0 \end{cases} \qquad \text{deterministic}$$

Inputs:

1. $\mu(x)$: Conditional success probability $\Pr(Y = 1 \mid x)$ ⟶

2. $v(x)$: Conditional sample size/confidence ⟶

3. $\bar{\gamma}(x)$: *Effective* discount factor ⟶

207 policy $\Pi^*$ ⟶ decision $a$

Inputs:

1.  $\mu$: Empirical success rate

2.  $\nu$: Number of acceptances

3.  $\bar{\gamma}$ = given discount factor $\gamma$

400

425

$X$ drawn from a finite domain $\mathcal{X}$, $|\mathcal{X}| < \infty$

Inputs:                                                          430

1.  $\mu(x)$: Empirical success rate conditioned on value $x$
2.  $\nu(x)$: Number of acceptances at $x$
3.  $\gamma(x)$: Effective discount factor that depends on probability $p(x)$ Proposed policy is optimal                    440                    435

Figure 5:
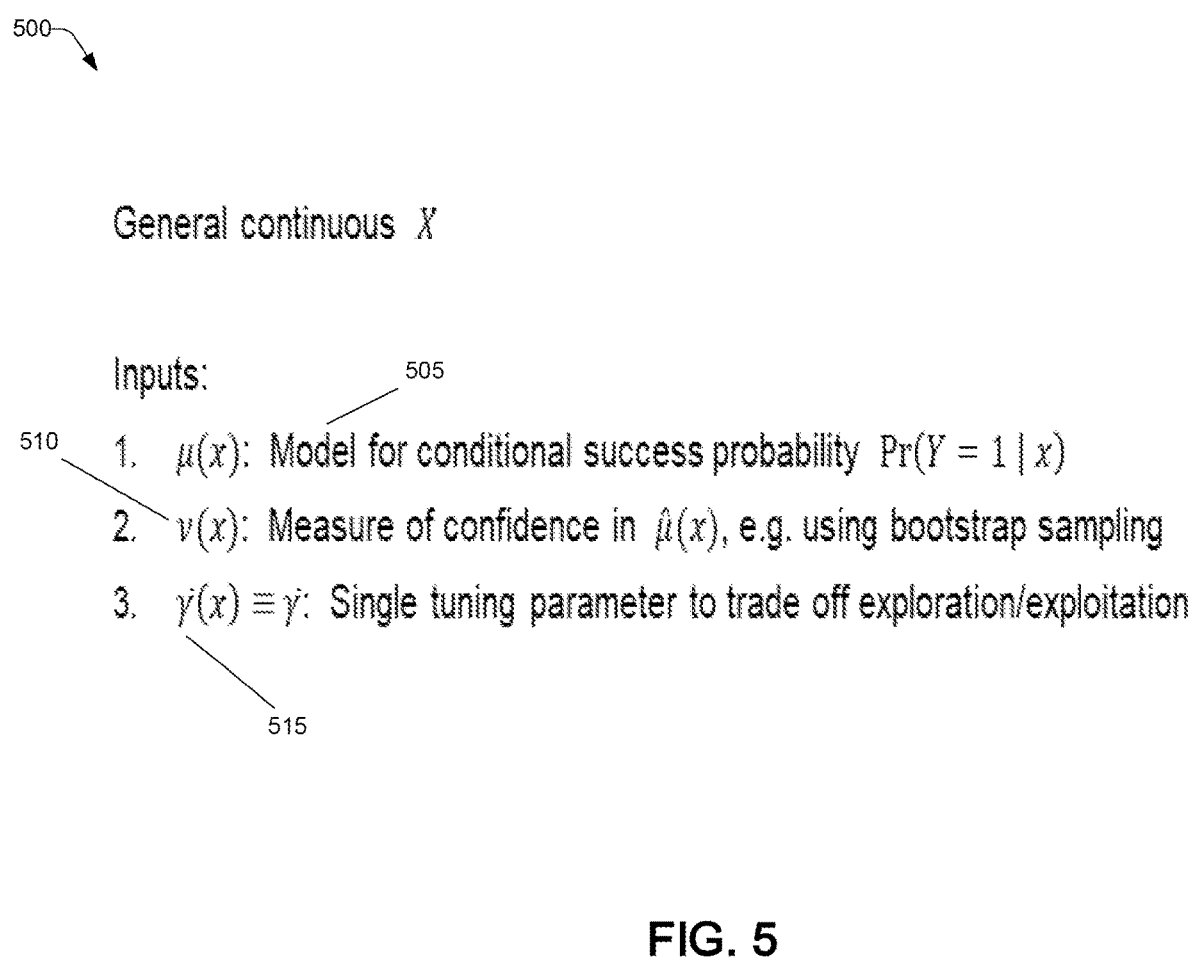

500

General continuous $X$

Inputs:      505

510   1.   $\mu(x)$: Model for conditional success probability $\Pr(Y = 1 \mid x)$ 2.   $v(x)$: Measure of confidence in $\hat{\mu}(x)$, e.g. using bootstrap sampling 3.   $\gamma(x) \equiv \gamma$: Single tuning parameter to trade off exploration/exploitation

START

RECEIVE A CONDITIONAL SUCCESS PROBABILITY VALUE OF A FEATURE
ASSOCIATED WITH AN ENTITY
805

RECEIVE A CONFIDENCE VALUE OF THE RECEIVED SUCCESS PROBABILITY
VALUE
815

DETERMINE A PARAMETER VALUE THAT IS A TRADE-OFF
820

RENDER A DECISION TO ACCEPT OR REJECT THE FEATURE
ASSOCIATED WITH THE ENTITY ACCORDING TO A MACHINE
LEARNING POLICY
825

END

900

DECISION MAKING MODULE
940

| SUCCESS PROBABILITY MODEL 942 | CONFIDENCE MODEL 944 | DISCOUNT FACOR MODEL 946 |
|---|---|---|
| POLICY MODEL 948 | CREDIT SCORE MODEL 950 | ML TRAINING MODEL 952 |

CPU
904

HDD
906

RAM/ROM
908

902

KEYBOARD
910

MOUSE
912

DISPLAY
914

COMM.
INTERFACE
916

1000

1054 C

1054 N

1050

1010

1054 A

1054 B

1100

DECISION-MAKING UNDER SELECTIVE LABELS

BACKGROUND

Technical Field

The present disclosure generally relates to systems and methods of machine learning and computerized decision making, and more particularly, to a computer-implemented method and system for decision making using selective labels.

Description of the Related Art

Selective labels are a feature of many high-stakes decision making applications. Selective labels arise from individuals receiving binary decisions, typically in the form of acceptance or rejection. Machine learning is employed to train a model in such decision-making applications.

In some applications, selective labels enable the making of decisions with no observed outcomes under one of the decisions. For example, if one is denied a requested pharmaceutical or biological treatment, there is no way to determine if the treatment had been approved whether such treatment would have been effective for a patient. In a case of deciding to restrict a license prior to a hearing, (or to deny credit), it cannot be determined from such decisions whether a person would have received an additional citation (or would have failed to repay a loan) as there no was opportunity provided to undertake such actions.

SUMMARY

In one embodiment, a computer-implemented method of decision-making using selective labels includes receiving a conditional success probability value of a feature associated with an entity; receiving a confidence value of the received success probability value. A parameter value is selected that is a trade-off between a short term learning and a long-term utility. A decision is rendered to accept or reject the feature associated with the entity according to a machine learning policy. The use of the trade-off parameter value accounts for the efforts of decisions taken during learning versus utility, and maximizes the discounted total reward.

In an embodiment, the machine learning policy for rendering the decision includes an optimal homogeneous policy, the feature associated with the entity is non-distinguishable from a population of other entities Properties of an optimal policy are derived. The optimal homogeneous policy does not require stochasticity.

In an embodiment, the machine learning policy for rendering the decision includes a homogeneous policy for rendering the decision to accept or reject based on the feature associated with the entity. A more accurate decision can result.

In an embodiment, the machine learning policy for rendering the decision includes a finite-domain case policy used for rendering the decision to accept or reject based on the feature associated with the entity over a finite number of values. The finite-domain case policy differs from the homogeneous case in that the effective discount factor accounts for the fact that arrivals of individuals are not equally separated by one time unit as in a homogeneous case but are separated by a random, geometrically distributed time.

In an embodiment, the machine learning policy for rendering the decision includes an infinite-domain case policy used for rendering the decision to accept or reject the feature associated with the entity. The infinite-domain case outperforms other baselines with less parameter sensitivity.

In an embodiment, the confidence value provides a confidence score of a conditional success probability value that considers a sample size of entities. A more accurate determination can be made based on knowledge of the sample size.

In an embodiment, the conditional success probability value and the confidence value are updated with a resultant outcome based on the decision to accept the feature associated with the entity. The resultant outcome is used to update the probability model and the confidence model.

In an embodiment, a machine learning model is trained to render the decision to accept or reject the feature associated with the entity. A more accurate outcome results from the machine learning model training.

In an embodiment, the entity includes multiple features, and the computer-implemented method further includes training a machine learning model to render the decision to accept or reject based on two or more of the multiple features associated with the entity. The decision to accept or reject based on multiple features provides increased accuracy.

In an embodiment, the machine learning policy is based on the determined trade-off parameter. The trade-off parameter accounts for the costs of decisions taken during learning and maximizes the discounted total reward.

In one embodiment, a computing device is configured for decision-making using selective labels includes a processor; a memory coupled to the processor, the memory storing instructions to cause the processor to perform acts including receiving a conditional success probability value of a feature associated with an entity. A confidence value of the received success probability value is received. A parameter value is selected that is a trade-off between a short term learning and a long-term utility. A decision is rendered to accept or reject the feature associated with the entity according to a machine learning policy. The use of the trade-off parameter value balances the efforts of decisions taken during learning versus utility, and maximizes the discounted total reward.

In an embodiment, the instructions cause the processor to perform an additional act of updating the conditional success probability value and the confidence value with a resultant outcome based on the decision to accept the feature associated with the entity. A more accurate decision can result.

In an embodiment, the instructions cause the processor to perform an additional act of training a machine learning model to render the decision to accept or reject the feature associated with the entity. More efficient results can occur.

In an embodiment, the instructions cause the processor to perform an additional act of training a machine learning model to render the decision to accept or reject based on two or more of the multiple features associated with the entity. Multiple features will provide for more accurate decisions.

In an embodiment, the instructions cause the processor to perform an additional act of rendering the decision to accept or reject based on an optimal homogeneous policy. The optimal homogeneous policy permits an initial case that is simpler, and then makes the policy more stringent as a rejection set increases.

In one embodiment, a computing device is configured to perform decision-making using selective labels. One or more processors including a dialog processor configured to process extracted text from a plurality of participants of a collaborative query. A memory is coupled to the one or more processors. A plurality of models are configured in the one or more processors including: a success probability model configured to provide an empirical success rate of a feature associated with an entity; and a confidence model configured to provide a confidence score of the empirical success rate considering a sample size of entities. A discount factor model is configured to select a parameter value that is a trade-off between a short term learning and a long-term utility. A policy model is configured for rendering a decision to accept or reject the feature associated with the entity, and to update the success probability model and the confidence model with a resultant outcome when the decision is accepted. More accurate decision making can result.

In an embodiment, the success probability model and the confidence model include a predictive model. Predictive models add flexibility to operation of the method.

In an embodiment, the success probability model is configured to render decisions for dispensing a requested pharmaceutical or biological treatment. More accurate treatment may result. The improved application of drugs can have a beneficial impact on health.

In an embodiment, the success probability model is configured for rendering decisions regarding suspending an operating license.

These and other features will become apparent from the following detailed description of illustrative embodiments thereof, which is to be read in connection with the accompanying drawings.

BRIEF DESCRIPTION OF THE DRAWINGS

The drawings are of illustrative embodiments. They do not illustrate all embodiments. Other embodiments may be used in addition to or instead. Details that may be apparent or unnecessary may be omitted to save space or for more effective illustration. Some embodiments may be practiced with additional components or steps and/or without all the components or steps that are illustrated. When the same numeral appears in different drawings, it refers to the same or like components or steps.

FIG. 2 is an overview of a computer-implemented method and device for decision-making using an optimal homogeneous policy, consistent with an illustrative embodiment.

FIG. 5 illustrates an example of an infinite-domain case for decision-making, consistent with an illustrative embodiment.

DETAILED DESCRIPTION

Overview

In the following detailed description, numerous specific details are set forth by way of examples to provide a thorough understanding of the relevant teachings. However, it should be understood that the present teachings may be practiced without such details. In other instances, well-known methods, procedures, components, and/or circuitry have been described at a relatively high level, without detail, to avoid unnecessarily obscuring aspects of the present teachings.

Figure 1:
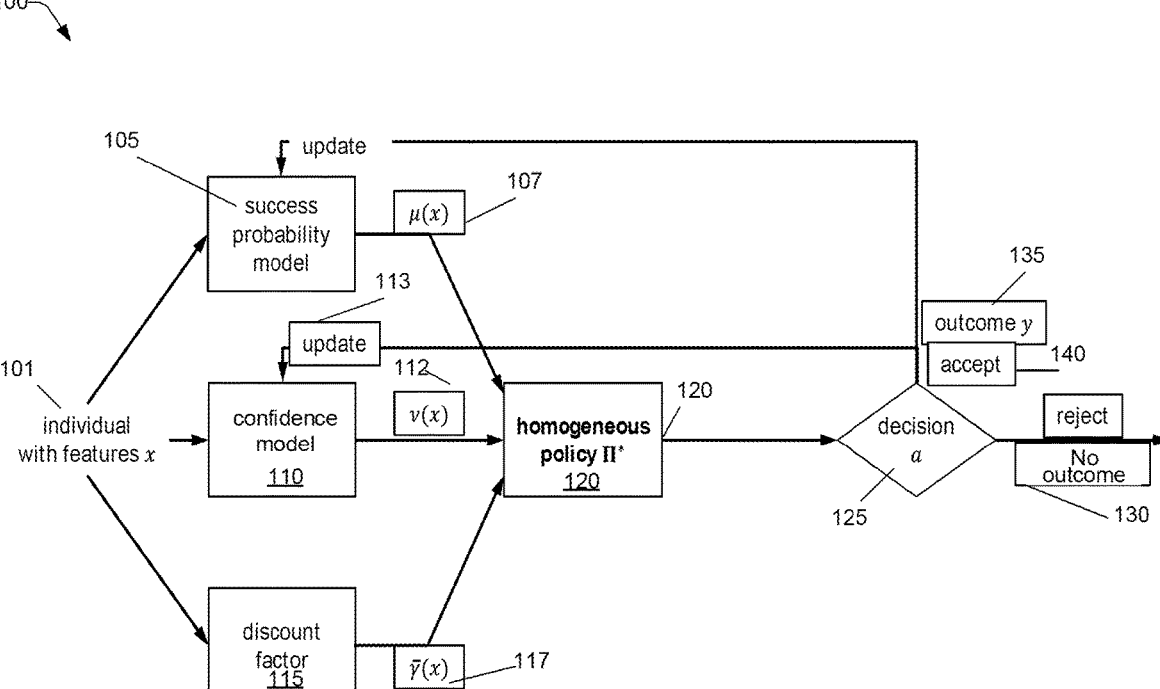
FIG. 1 is an architectural overview of a computer-implemented device and a computer-implemented method for decision-making, consistent with an illustrative embodiment.

FIG. 1 is an architectural overview 100 of a computer-implemented device and computer-implemented method for decision-making, consistent with an illustrative embodiment. It is to be understood that the present disclosure is not limited to the drawings, as there may be fewer elements or more elements than shown and described. According to an aspect of the present disclosure, a computer-implemented device and method for decision making under selective labels uses a machine learning model that balances learning costs against future utility. Optimal decision polices are formulated for one or more of homogeneous cases and finite domain cases of a selective labels problem. These optimal decision polices can be extended to a general infinite domain case to thereby provide superior results. Such decision policies account for the cost of learning while seeking to maximize utility.

In an embodiment, the decision-making approach is to solve a relatively simple special case and then explore the extent to which such solution can be used in a more generalized scenario. For example, individuals can be drawn from a homogeneous population without distinguishing features. By applying dynamic programming, an optimal acceptance policy is shown as a threshold policy applied to an estimated probability of success. The properties of the optimal acceptance policy are derived. As more observations are collected, the policy becomes more stringent (e.g., an increased rejection set).

Referring to FIG. 1, an individual 101 (with feature x) has submitted a request that will be decided according to the computer-implemented method. There are three models 105, 110, 115 shown as inputs to a homogeneous policy 120 (in this illustrative embodiment). The models include a success probability model 105, a confidence model 110, and a discount factor model 115. The success probability model 105 is symbolized by u(x) 107, the confidence model 110 by v(x) 112, and the discount factor 115 by ỹ(x) 117. It is to be understood herein that u, v and ỹ correspond to the Greek letters mu, nu and gamma, respectively.

The policy 120 is used to analyze the inputs and results in a decision 125. The decision can result in a rejection (no outcome 130), or an acceptance 140 with a trackable outcome 135. The success probability model 105 and the confidence model 110 are updated with the acceptance result. There is a more detailed discussion regarding these models in the detailed description, particularly with reference to the flow chart of FIG. 8.

A selective labels problem is simulated in the disclosure in which features xi of individuals are examined one by one and only revealing the outcome yi if the decision is to accept.

In addition, to provide an initial training (e.g., exploration) set, the first B0 individuals are always accepted and their outcomes are observed. Notably, the rewards/costs incurred from collecting this training data are counted toward the total utility. The objective of utility is quantified by the expectation of the discounted infinite sum of rewards for some discount factor <1, $$E[\Sigma_{i=0}^{\infty} \gamma^i a_i (y_i - c)] = E[\Sigma_{i=0}^{\infty} \gamma^i \Pi(x_i)(\rho(x_i) - c)] \qquad \text{(Eqn. 1)}$$

Where there is defined the conditional success probability $\rho(x) = \rho(Y=1|x)$, and i is an index over individuals, $\gamma$ is the discount factor <1, $a_i$ is the decision for individual, c is a constant corresponding to the reward of success/cost of failure, and $\Pi$ is the decision policy.

The right-hand side of equation (1) results from taking the conditional expectation given xi, leaving an expectation over xi~p(x). The right-hand expectation indicates that the problem of the determining policy $\Pi(x)$ can be decomposed (at least conceptually) over values of X. This decomposition is clearest in the case of a discrete domain X, for which the expectation is a sum, weighted by p(x). The decomposition motivates the study of a simpler problem in which x is fixed or dropped, resulting in a homogeneous population.

By virtue of the teachings herein, the computer-implemented method and computer device of the present disclosure provides an improvement in computer operations and in computer-implemented decision making using selective labels. For example, more accurate decision-making has an impact in virtually all applications. Also, there can be fewer iterations and computer usage because of more accurate decisions, resulting in decreased processing overhead and storage realized, as well as a reduction in power consumed. Still further, the training of the models is also more efficient, which provides results in less time. Additional advantages of the computer-implemented method and device of the present disclosure are disclosed herein.

Example Embodiments

FIG. 2 is an overview 200 of a computer-implemented method and device for decision-making using an optimal homogeneous policy, consistent with an illustrative embodiment. In FIG. 2, the decision 201 is made using an optimal homogeneous policy 207 (may be similar to the policy 120 shown in FIG. 1). A value function 203 is computed by recursion, and then a threshold 205 is applied deterministically.

The value function in this example is $V^*(\mu(x), v(x); \bar{\gamma}(x))$, where the values input to the policy 207 include (1) u(x), which is the conditional success probability Pr (Y=1x); (2) v(x), the conditional sample size/confidence; and (3) $\bar{y}(x)$, the effective discount factor. The decision 209 may then be used to update u and v as shown in FIG. 1.

The threshold 205 (for policy 207), which is deterministic, is as follows:

$$\Pi^*(\mu(x), v(x); \bar{\gamma}(x)) = \begin{cases} 1, & V^*(\mu(x), v(x); \bar{\gamma}(x)) > 0 \\ 0, & V^*(\mu(x), v(x); \bar{\gamma}(x)) \le 0 \end{cases} \qquad \text{(Eqn. 2)}$$

For a homogeneous selective labels problem, the optimal acceptance policy that maximizes discounted total reward (1) is a threshold policy. A graphical illustration of the homogeneous case is provided in FIG. 3.

Figure 3:
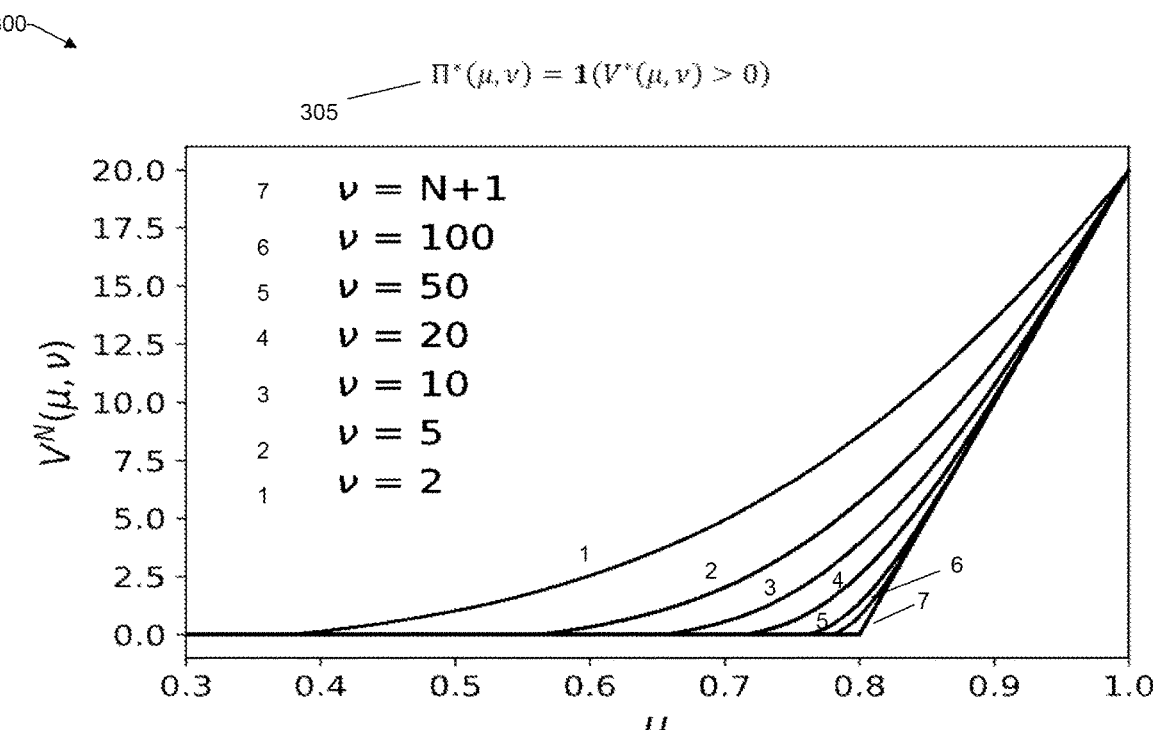
FIG. 3 a graphical illustration of a homogenous case for decision-making, consistent with an illustrative embodiment.

FIG. 3 is a graphical illustration of a homogenous case 300 for decision-making, consistent with an illustrative embodiment. The function $V^*(\mu, v)$ is plotted, with the result of the computation for N=1000, c=0:8, and $\gamma$=0:99. The plot suggests that $V^N(u,v) \ge V^N(u,v+1)$ and that $V^N(u,v)$ is a non-decreasing convex function of u for all v. It also shows that $V^N(u,v)$ is quite close to $V^N(u, 1001)=V^*(u, \infty)$ for large v>100.

Figure 4:
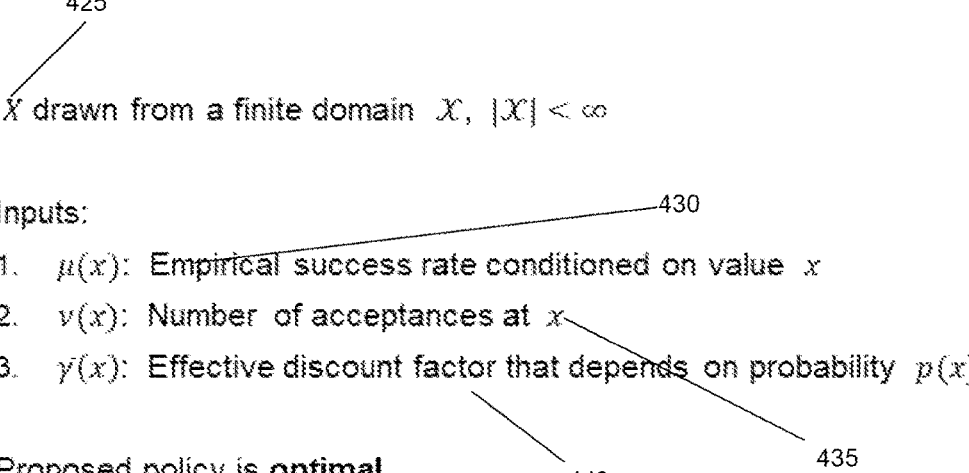
FIG. 4 illustrates an example of a finite-domain case for decision-making, consistent with an illustrative embodiment.

FIG. 4 illustrates an example of a finite-domain case 400 for decision-making, consistent with an illustrative embodiment. For the finite-domain case 425, X is drawn from a finite domain X, $|X| < \infty$. The conditional means u(x) 430 can be well-estimated by the respective empirical means and a model is not needed. Following a Bayesian approach of placing a beta prior on the success probability u(x) 430, these empirical means are slightly modified by adding pseudo-counts from the prior executions. The inputs shown are u(x), the empirical success rate conditioned on the value x, v(x) 435, the number of acceptances at x, and $\tilde{y}(x)$, the effective discount factor 440 that depends on probability p(x).

With regard to the finite domain case, the features "X" are present and take a finite number of values. The decomposability of eqn. (1) into a sum over x∈X implies that the optimal decision policy comprises multiple optimal homogeneous policies in parallel, one for each x∈X Accordingly, a beta distribution is now posited for each conditional success probability $\rho(x)$, parametrized by state variables u(x) and v(x): v(x) is the number of acceptances with feature value x, plus pseudo-counts from the prior on $\rho(x)$, while u(x) is the fraction of successes among acceptances at x, again accounting for prior pseudo-counts. The difference with respect to the homogeneous case is that the effective discount factor seen at each value x is not equal to the $\gamma$ in eqn. (1) but depends on x as follows:

$$\bar{y}(x) = \frac{\gamma p(x)}{1 - \gamma(1 - p(x))} \qquad \text{(Eqn. 3)}$$

Where p(x) is the probability of feature value x.

FIG. 5 illustrates an example of an infinite-domain case 500 for decision-making, consistent with an illustrative embodiment. For the general infinite-domain case, the homogeneous policy is extended by using a probabilistic classifier and bootstrapping to provide its inputs. The inputs shown are the model for conditional success probability 505, the measure of confidence 510 and a single tuning parameter to trade off exploration/exploitation 515.

Figure 6:
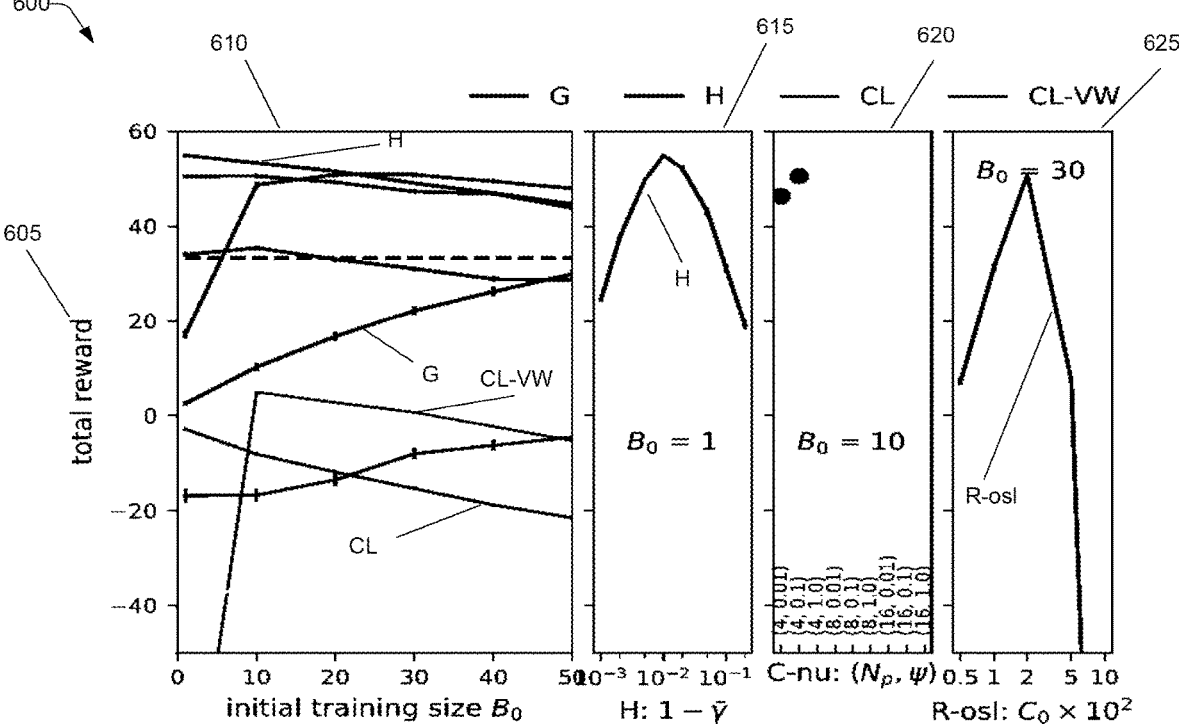
FIG. 6 illustrates an example of the utility of a computer-implemented method and device for decision-making using a first dataset, consistent with an illustrative embodiment.

FIG. 6 illustrates an example of the utility of a computer-implemented method and device for decision-making using a first dataset, consistent with an illustrative embodiment. The first dataset, which in a non-limiting example, is a pharmaceutical and/or biological treatment dispensing dataset, which is used for requests for a particular medication. Acceptance corresponds to approving a patient to receive the requested prescription drug or biologic at the requested dosage. Each dataset is randomly permuted 1000 times and means and standard errors are computed from these permutations.

FIG. 6 plots the total rewards 605 attained on the dataset without discounting ($\gamma$=1) versus various items, such as the initial training size in graph 610. The shapes of the curves as functions of an initial training size B0. There are some additional algorithms that benefit from having B0>0.

A salient difference compared to the finite-domain case is that the greedy policy (G) shown in graph 610 is more competitive. In FIG. 6, graph 610 shows H is the only policy that consistently exceeds the largest total reward achieved by G, as B0 is allowed to increase. Conversely, CL, CL-VW, and EG never exceed the maximum reward of G, suggesting that they over-explore using an acceptance rate that is too high. The VW variant CL-VW outperforms CL on the financial dataset except at B0=1 (graph 610), justifying the alternative implementation. Graph 615 shows that the homogeneous policy (H) achieves relatively high total reward over a wide range of its parameter \bar\{gamma\}. In contrast, R-osl in graph 625 shows the utility is much lower for C0 grid values not equal to the best one. C-nu (graph 620) can display extreme sensitivity.

Figure 7:
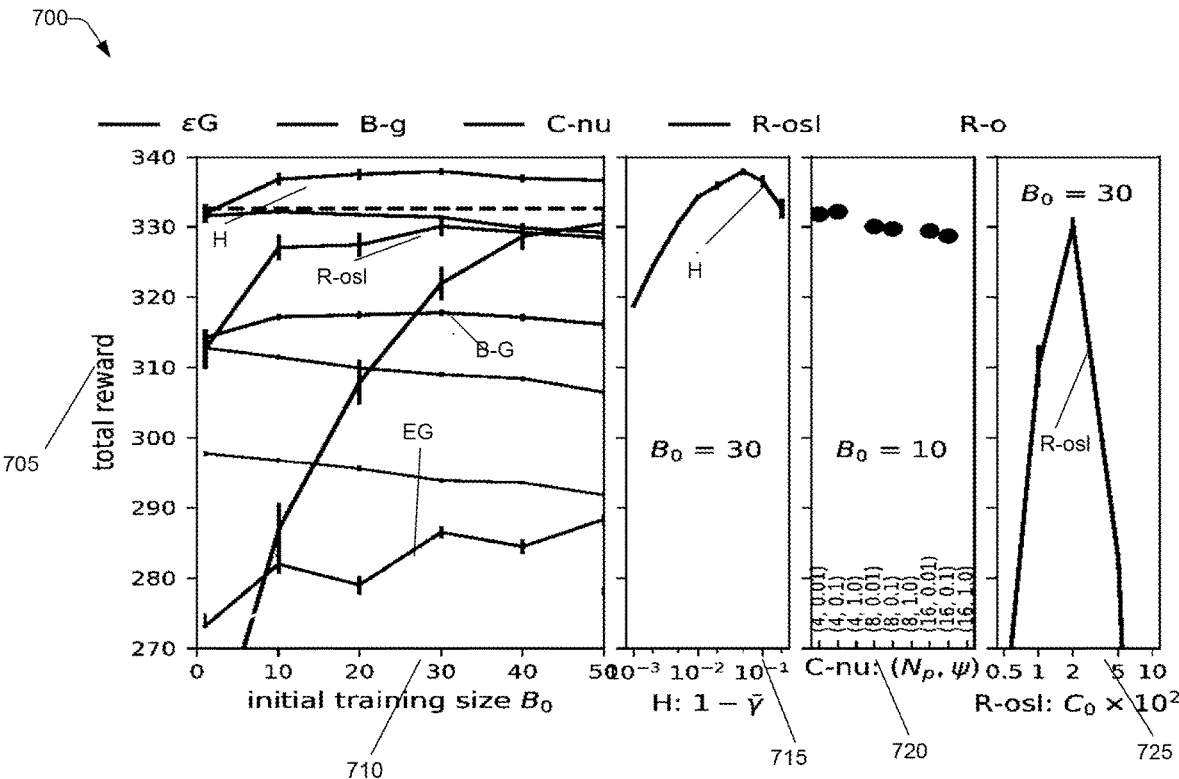
FIG. 7 illustrates an example of the utility of a computer-implemented method and device for decision-making using a second dataset, consistent with an illustrative embodiment.

FIG. 7 illustrates a graphical example 700 of the utility of a computer-implemented method and device for decision-making using a second dataset, consistent with an illustrative embodiment. It is to be understood that the applications of the present disclosure and the appended claims are not limited to the examples provided for illustrative purposes.

With reference to FIG. 7, the second dataset includes demographics and histories of motorists who received traffic citations, a recidivism risk score produced by a dataset tool, and an outcome variable indicating whether the motorist received another traffic citation within two years of a previous offense. Acceptance corresponds to letting an offender continue to operate a vehicle awaiting disposition of a current offense, and rejection corresponds to a suspension of the motorist's license pending a hearing. Similar to FIG. 6, each dataset is randomly permuted 1000 times and means and standard errors are computed from these permutations. FIG. 7 plots the total rewards 705 attained on the dataset without discounting ($\gamma$=1) versus various items, such as the initial training size in graph 710. The shapes of the curves as functions of an initial training size B0. There are some additional algorithms that benefit from having B0>0.

The highest utility is again achieved by a policy in the homogeneous family, namely the policy labelled H. Next in line are R-osl and C-nu. All three policies have at least one algorithm-specific parameter (discount factory $\tilde{y}$ for H, C0 for R-osl, (Np; $\psi$) for C-nu) as well as the online learning rate that are tuned. The panel 715 in FIG. 7 shows that H is less sensitive to its parameter, achieving good performance over a relatively wide range of $\gamma$. In contrast, R-osl in graph 725 shows the utility is much lower for C0 grid values not equal to the best one. C-nu can display extreme sensitivity. In FIG. 7, panel 720, $\psi$=1 drops the total reward outside the plotted range.

It is also understood that there are many applications in addition to the aforementioned examples, including but not in any way limited to sentencing guidelines, credit worthiness, providing network resources, managing an electric power grid, etc.

Example Process

Figure 8:
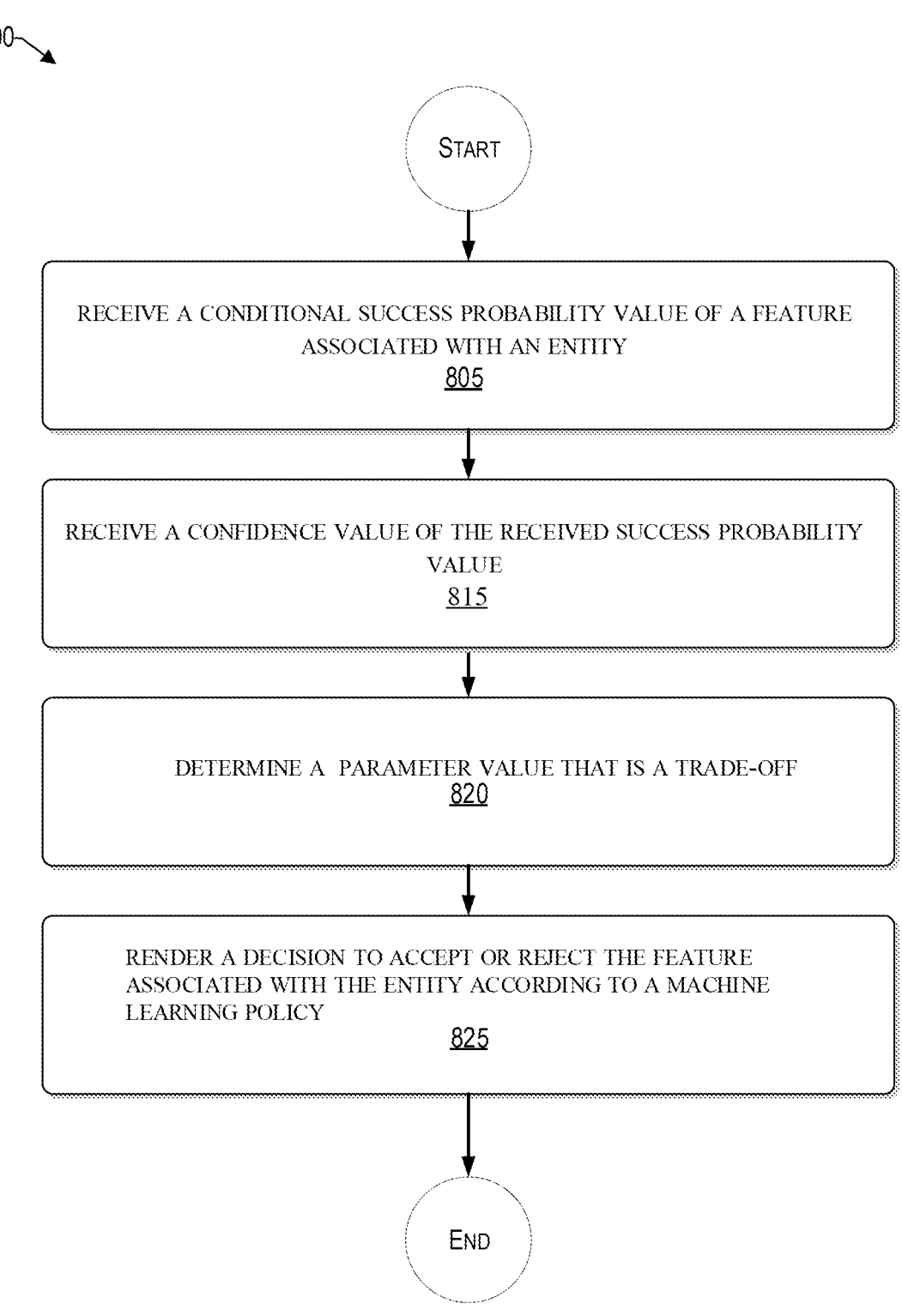
FIG. 8 is a flowchart illustrating a non-exhaustive example of a computer-implemented method, consistent with an illustrative embodiment.

With the foregoing overview of the example architecture, it may be helpful now to consider a high-level discussion of an example process. To that end, FIG. 8 is a flowchart illustrating a computer-implemented method of automatically performing and incrementally specifying queries through dialog understanding in real time, consistent with an illustrative embodiment. FIG. 8 is shown as a collection of blocks, in a logical order, which represents a sequence of operations that can be implemented in hardware, software, or a combination thereof. In the context of software, the blocks represent computer-executable instructions that, when executed by one or more processors, perform the recited operations. Generally, computer-executable instructions may include routines, programs, objects, components, data structures, and the like that perform functions or implement abstract data types. In each process, the order in which the operations are described is not intended to be construed as a limitation, and any number of the described blocks can be combined in any order and/or performed in parallel to implement the process.

At operation 805, a conditional success probability value of a feature associated with an entity is received (see FIG. 1). Alternatively, the value can be retrieved from storage, or calculated. A decision to accept or reject is made based on each individual's feature(s) according to a decision policy. The conditional success probability value is the estimated probability of success if the individual is accepted.

At operation 815, a confidence value of the success probability is received. The confidence value may be based in part on a sample size of the probability value. The number of labels observed for a feature x may be seen as a measure of confidence.

At operation 820, a trade-off parameter value is selected as a third input along with the received conditional success probability value of a feature and the confidence value. The trade-off parameter accounts for the efforts associated with learning as the method seeks to maximize utility. In maximizing utility, deterministic decisions are made and the decisions can become more stringent as more labels are observed, and the sample size to render a decision increases.

At 825, a decision is rendered to accept or reject the feature associated with the entity according to a machine learning policy. In an embodiment, the decision is output to one or more recipients, such as an entity which requested the decision. For example, in the case of a credit application, the lender and the potential borrower may receive the information regarding approval or denial. With reference to FIG. 1, it is shown that there can be an update of the success probability model 105 and or the confidence model 110 with the outcome 135, particularly in the case of acceptance.

The above computer-implemented method has many varied applications beyond the embodiments shown and described. For example, a medical diagnosis system can use selective labels to approve or deny a request for medications, or medical tests, with a follow-up if the request is accepted or requested. When the decision-making is related to approving credit, the decision-maker's rewards are fairly clear. Such rewards include interest earned in the case of success (repayment), loss of principal (or some expected fraction thereof) in the case of failure (default), and little to no cost for rejection. The individual's rewards may also be taken into account although harder to quantify, for example, accomplishing the objective of the request (e.g., owning a home) or damage to creditworthiness from a default. In additional embodiments, there can be a teaching through machine learning of the cost of rejection through an alternative feedback mechanism. For example, there can be a follow up with a subset of its rejected applicants to understand the impact on the lives of such applicants. In any case, once the three reward values are determined, they can then be linearly transformed to 1−c, −c, and 0 (respectively representing a reward of 1−c if acceptance leads to success, −c if acceptance leads to failure, and 0 if the individual is rejected) without a loss of generality.

Example Particularly Configured Computer Hardware Platform

Figure 9:
FIG. 9 is a functional block diagram illustration of a particularly configured computer hardware platform, consistent with an illustrative embodiment.

FIG. 9 provides a functional block diagram illustration 900 of a computer hardware platform. In particular, FIG. 9 illustrates a particularly configured network or host computer platform 900, as may be used to implement the method shown in FIG. 8.

The computer platform 900 may include a central processing unit (CPU) 904, a hard disk drive (HDD) 906, random access memory (RAM) and/or read-only memory (ROM) 908, a keyboard 910, a mouse 912, a display 914, and a communication interface 916, which are connected to a system bus 902. The HDD 906 can include data stores.

In one embodiment, the HDD 906 has capabilities that include storing a program that can execute various processes, such as machine learning.

In FIG. 9, there are various modules shown as discrete components for ease of explanation. However, it is to be understood that the functionality of such modules and the quantity of the modules may be fewer or greater than shown. It is to be understood that the modules shown and described herein can be trained by machine learning both to train and update their various operations.

The decision-making module 940 is configured to control the operation of the modules 942-952, consistent with an illustrative embodiment. The success probability model 942 is configured to provide an empirical success rate of a feature associated with an entity. The confidence model 944 is configured to provide a confidence score of the empirical success rate considering a sample size of entities. A discount factor model 946 is configured to select a parameter value comprising a trade-off between a short term learning and a long-term utility. A policy model 948 is configured to render a decision to accept or reject the feature associated with the entity, and to update the success probability model and the confidence model with a resultant outcome when the decision is accepted. The credit score model 950 is executed in conjunction with the decision-making model 940 to determine, for example, whether an individual is creditworthy, and to monitor an impact if a loan is made and paid on time or not paid, paid late, etc. The Machine Learning training 952 model can be trained to render the decision to accept or reject a feature associated with the entity, as discussed herein above.

Example Cloud Platform

As discussed above, functions relating to the low bandwidth transmission of high-definition video data may include a cloud. It is to be understood that although this disclosure includes a detailed description of cloud computing as discussed herein below, implementation of the teachings recited herein is not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service-oriented with a focus on statelessness, low coupling, modularity, and semantic interoperability. At the heart of cloud computing is an infrastructure that includes a network of interconnected nodes.

Figure 10:
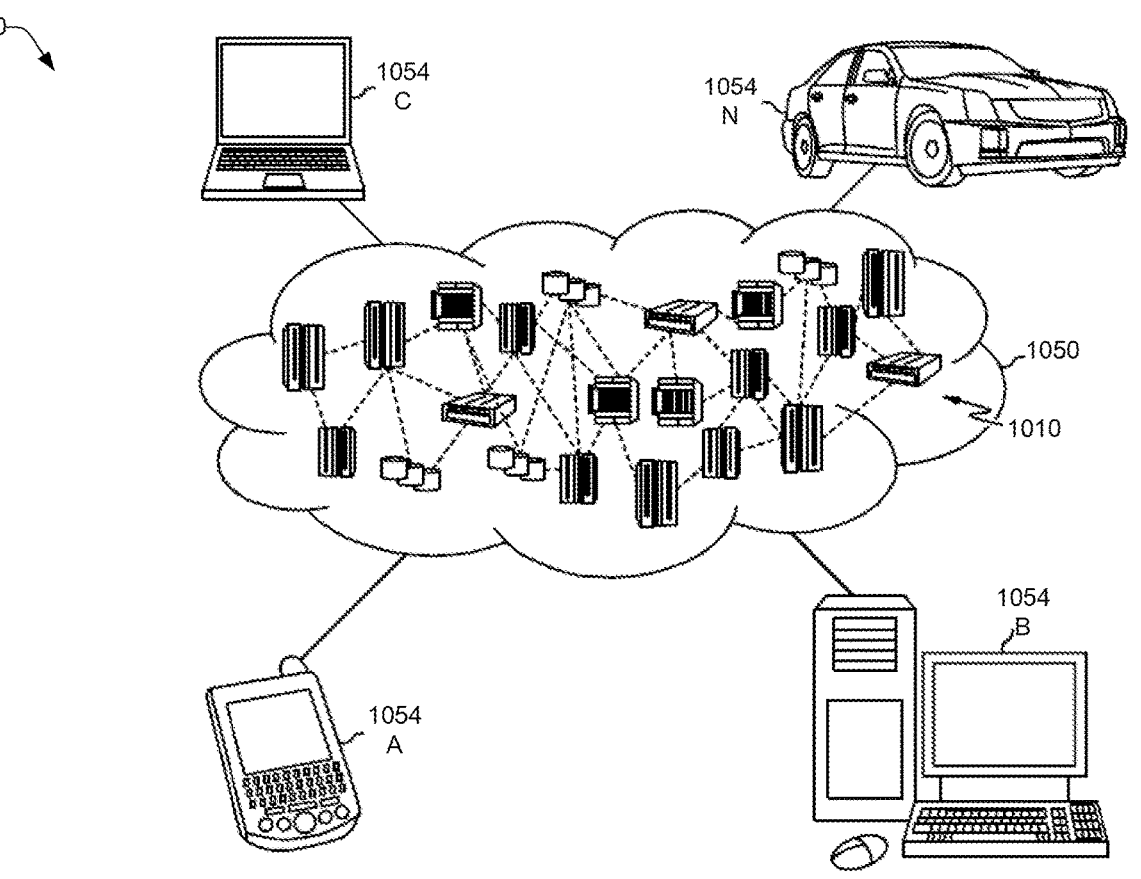
FIG. 10 depicts an illustrative cloud computing environment, consistent with an illustrative embodiment.

Referring now to FIG. 10, an illustrative cloud computing environment 1000 utilizing cloud computing is depicted. As shown, cloud computing environment 1000 includes cloud 1050 having one or more cloud computing nodes 1010 with which local computing devices used by cloud consumers, such as, for example, personal digital assistant (PDA) or cellular telephone 1054A, desktop computer 1054B, laptop computer 1054C, and/or automobile computer system 1054N may communicate. Nodes 1010 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms, and/or software as services for which a cloud consumer does not need to maintain resources on a local computing device. It is understood that the types of computing devices 1054A-N shown in FIG. 10 are intended to be illustrative only and that computing nodes 1010 and cloud computing environment 1000 can communicate with any type of computerized device over any type of network and/or network addressable connection (e.g., using a web browser).

Figure 11:
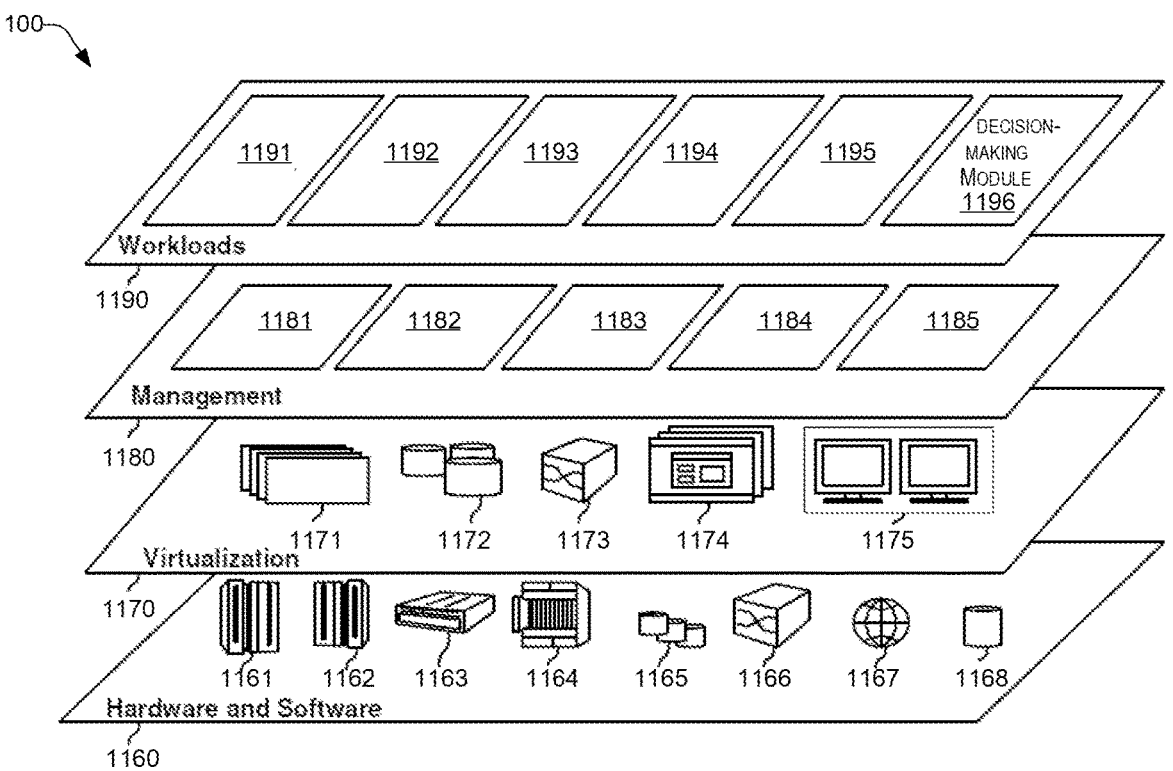
FIG. 11 depicts a set of functional abstraction layers provided by a cloud computing environment, consistent with an illustrative embodiment.

Referring now to FIG. 11, a set of functional abstraction layers 1100 provided by cloud computing environment 1000 (FIG. 10) is shown. It should be understood in advance that the components, layers, and functions shown in FIG. 11 are intended to be illustrative only and embodiments of the disclosure are not limited thereto. As depicted, the following layers and corresponding functions are provided:

Hardware and software layer 1160 include hardware and software components. Examples of hardware components include: mainframes 1161; RISC (Reduced Instruction Set Computer) architecture-based servers 1162; servers 1163; blade servers 1164; storage devices 1165; and networks and networking components 1166. In some embodiments, software components include network application server software 1167 and database software 1168.

Virtualization layer 1170 provides an abstraction layer from which the following examples of virtual entities may be provided: virtual servers 1171; virtual storage 1172; virtual networks 1173, including virtual private networks; virtual applications and operating systems 1174; and virtual clients 1175.

In one example, management layer 1180 may provide the functions described below. Resource provisioning 1181 provides dynamic procurement of computing resources and other resources that are utilized to perform tasks within the cloud computing environment. Metering and Pricing 1182 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1183 provides access to the cloud computing environment for consumers and system administrators. Service level management 1184 provides cloud computing resource allocation and management such that required service levels are met. Service Level Agreement (SLA) planning and fulfillment 1185 provide pre-arrangement for, and procurement of, cloud computing resources for which a future requirement is anticipated in accordance with an SLA.

Workloads layer 1190 provides examples of functionality for which the cloud computing environment may be utilized. Examples of workloads and functions which may be provided from this layer include: mapping and navigation 1191; software development and lifecycle management 1192; virtual classroom education delivery 1193; data analytics processing 1194; transaction processing 1195; and module 1196 configured to decision making, as discussed herein above.

Conclusion

The descriptions of the various embodiments of the present teachings have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing has described what are considered to be the best state and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications, and variations that fall within the true scope of the present teachings.

The components, operations, steps, features, objects, benefits, and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently.

The flowchart, and diagrams in the figures herein illustrate the architecture, functionality, and operation of possible implementations according to various embodiments of the present disclosure.

While the foregoing has been described in conjunction with exemplary embodiments, it is understood that the term "exemplary" is merely meant as an example, rather than the best or optimal. Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any such actual relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments have more features than are expressly recited in each claim. Rather, as the following claims reflect, the inventive subject matter lies in less than all features of a single disclosed embodiment. Thus, the following claims are hereby incorporated into the Detailed Description, with each claim standing on its own as a separately claimed subject matter.

What is claimed is:

1. A computer-implemented method of automatic decision-making using selective labels, the method comprising:
   receiving, at a success probability model of a computing device, a feature vector associated with an entity and generating, via the success probability model analyzing the feature vector, a conditional success probability value representing a likelihood of success of a feature associated with the entity if the entity is accepted;
   receiving, at a confidence model of the computing device, a sample size associated with prior accepted entities having similar features and generating, via the confidence model analyzing the sample size, a confidence value associated with the conditional success probability value;
   determining, at a discount factor model of the computing device, a tuning parameter value that is <1 and that represents a trade-off between a short-term learning cost and a long-term utility;
   rendering a decision, using a policy model of the computing device, to accept the entity based on a threshold function of the conditional success probability value, the confidence value, and the tuning parameter value; and
   iteratively updating the success probability model and the confidence model using an observed outcome that results from accepting the entity.

2. The computer-implemented method of claim 1, wherein:
   the machine learning policy for rendering the decision comprises an optimal homogeneous policy; and
   the feature associated with the entity is non-distinguishable from a population of other entities.

3. The computer-implemented method of claim 1, wherein the machine learning policy for rendering the decision comprises a homogeneous policy for rendering the decision to accept based on the feature associated with the entity.

4. The computer-implemented method of claim 1, wherein the machine learning policy for rendering the decision comprises a finite-domain case policy used for rendering the decision to accept based on the feature associated with the entity.

5. The computer-implemented method of claim 1, wherein the machine learning policy for rendering the decision comprises an infinite-domain case policy used for rendering the decision to accept the feature associated with the entity.

6. The computer-implemented method of claim 1, further comprising updating the policy model based on the observed outcome that results from accepting the entity.

7. The computer-implemented method of claim 1, further comprising training a machine learning model to render the decision to accept the feature associated with the entity.

8. The computer-implemented method of claim 1, wherein the entity includes multiple features, and the computer-implemented method further comprises training a machine learning model to render the decision to accept based on two or more of the multiple features associated with the entity.

9. The computer-implemented method of claim 1, wherein the machine learning policy is based on the conditional success probability value and the confidence value.

10. A computing device configured for decision-making using selective labels, the computing device comprising:
   a processor,
   a memory coupled to the processor, the memory storing instructions to cause the processor to perform acts comprising:
   receiving, at a success probability model of a computing device, a feature vector associated with an entity and generating, via the success probability model analyzing the feature vector, a conditional success probability value representing a likelihood of success of a feature associated with the entity if the entity is accepted;
   receiving, at a confidence model of the computing device, a sample size associated with prior accepted entities having similar features and generating, via the confidence model analyzing the sample size, a confidence value associated with the conditional success probability value;
   determining, at a discount factor model of the computing device, a tuning parameter value that is <1 and that represents a trade-off between a short-term learning cost and a long-term utility;
   rendering a decision, using a policy model of the computing device, to accept the entity based on a threshold function of the conditional success probability value, the confidence value, and the tuning parameter value; and
   iteratively updating the success probability model and the confidence model using an observed outcome that results from accepting the entity.

11. The computing device of claim 10, wherein the instructions cause the processor to perform an additional act of training a machine learning model to render the decision to accept the feature associated with the entity.

12. The computing device of claim 10, wherein the instructions cause the processor to perform an additional act of training a machine learning model to render the decision to accept based on two or more of the features associated with the entity.

13. The computing device of claim 10, wherein the instructions cause the processor to perform an additional act of rendering the decision to accept based on an optimal homogeneous policy.

14. A computing device configured to perform decision-making using selective labels, the computing device comprising:

one or more processors including a dialog processor configured to process extracted text from a plurality of participants of a collaborative query;

a memory coupled to the one or more processors;

a plurality of models configured in the one or more processors, the plurality of models comprising:

a success probability model configured to provide a conditional success probability value representing an empirical success rate of a feature associated with an entity;

a confidence model configured to provide a confidence value of the conditional success probability value, based at least on a sample size of entities;

a discount factor model configured to determine a tuning parameter value that is <1 and that represents a trade-off between a short-term learning cost and a long-term utility; and a policy model configured to render a decision to accept the feature associated with the entity based on a threshold function of the conditional success probability value, the confidence value, and the tuning parameter value; and iteratively update the success probability model and the confidence model with a resultant outcome when the decision is to accept.

15. The computing device according to claim 14, wherein the success probability model and the confidence model each comprise a predictive model.

16. The computing device according to claim 14, wherein the success probability model is configured for automatically rendering decisions for dispensing a requested pharmaceutical or biological treatment.

17. The computing device according to claim 14, wherein the success probability model is configured for rendering decisions regarding suspending an operating license.

* * * * *